(12) United States Patent
Stoddart et al.

(10) Patent No.: US 9,828,371 B2
(45) Date of Patent: Nov. 28, 2017

(54) METHODS OF MAKING DIAZAPEROPYRENIUM DICATIONS AND USES THEREOF

(71) Applicant: Northwestern University, Evanston, IL (US)

(72) Inventors: J. Fraser Stoddart, Evanston, IL (US); Ashish N. Basuray, Chicago, IL (US); Karel J. Hartlieb, Evanston, IL (US); Srinivasan Sampath, Daejeon (KR); Henri-Pierre Jacquot de Rouville, Saint-Etienne de Fougeres (FR)

(73) Assignee: NORTHWESTERN UNIVERSITY, Evanston, IL (US)

( * ) Notice: Subject to any disclaimer, the term of this patent is extended or adjusted under 35 U.S.C. 154(b) by 515 days.

(21) Appl. No.: 14/499,074

(22) Filed: Sep. 26, 2014

(65) Prior Publication Data

US 2016/0368913 A1 Dec. 22, 2016

Related U.S. Application Data

(60) Provisional application No. 61/883,352, filed on Sep. 27, 2013.

(51) Int. Cl.
*C07D 471/04* (2006.01)
*C01B 31/04* (2006.01)

(52) U.S. Cl.
CPC ........ *C07D 471/04* (2013.01); *C01B 31/0469* (2013.01)

(58) Field of Classification Search
CPC .................. C01B 31/0469; C07D 471/04
See application file for complete search history.

(56) References Cited

PUBLICATIONS

Sampath, et al., Direct Exfoliation of Graphite to Graphene in Aqueous Media with Diazoperopyrenium Dictations, Adv. Mater. 2013; 25: 2740-2745, Supplementary Information S1-S11 (published online Apr. 3, 2013).*
Basuray, et al., The Chameleonic Nature of Diazaperopyrenium Recognition Processes, Agnew. Chem. Ind. Ed. 2002; 51:11872-11877.*
Basuray, et al., The Chameleonic Nature of Diazaperopyrenium Recognition Processes, Agnew. Chem. Ind. Ed. 2012; 51:11872-11877 (published online Sep. 28, 2012).*
Basuray, A.N, Jacquot de Rouville, H.-P., Hartlieb, K.J., Kikuchi, T., Strutt, N.L., Bruns, C.J., Ambrogio, M.W., Avestro, A.-J., Schneebeli, S.T., Fahrenbach, A.C., Stoddart, J.F. "The Chameleonic Nature of Diazaperopyrenium Recognition Processes," Angew. Chem. Int. Ed. 2012, 51, 11872-11877.
Basuray, A.N., Jacquot de Rouville, H.-P., Hartlieb, K.J., Fahrenbach, A.C., Stoddart, J.F. "Beyond Perylene Diimides—Diazaperopyrenium Dications as Chameleonic Nanoscale Building Blocks," Chem. Asian. J. 2013, 8:512-532.
Che, et al. "Ultralong Nanobelts Self-Assembled from an Asymmetric Perylene Tetracarboxylic Diimide" J. Am. Chem. Soc. 2007, 23, 7234-7235.

(Continued)

*Primary Examiner* — Daniel C McCracken
(74) *Attorney, Agent, or Firm* — Klintworth & Rozenblat IP LLP

(57) ABSTRACT

Methods of making diazaperopyrenium dications with 2,3-dichloro-5,6-dicyano-1,4-benzoquinone, and uses thereof are provided.

20 Claims, 9 Drawing Sheets

(56) References Cited

PUBLICATIONS

Hartlieb, K.J., Basuray, A.N., Ke, C., Sarjeant, A.A., Jacquot de Rouville, H.-P., Kikuchi, T., Forgan, R.S., Kurutz, J.W., Stoddart. J.F. "Chameleonic binding of the dimethyldiazaperopyrenium dication by cucurbit[8]uril," Asian J. Org. Chem. 2013, 2, 225-229.

Sampath, S., Basuray, A.N., Hartlieb, K.J., Aytun, T., Stupp, S.I., Stoddart, J.F. "Direct Exfoliation of Graphite to Graphene in Aqueous Media with Diazaperopyrenium Dications," Adv. Mater. 2013, 25, 2740-2745.

Stang, et al. "Self-Assembly of Cationic, Tetranuclear, Pt(II) and Pd(II) Macrocyclic Squares.X-ray Crystal Structure of [Pt 2+(dppp)(4,4'-bipyridyl)2-OSO2CF3]4" J. Am. Chem. Soc. 1995, 117, 6273-6283.

Xie, et al. "Self-Assembled Photoactive Polyelectrolyte/Perylene-Diimide Composites" Langmuir 2005, 21, 4149-4155.

\* cited by examiner

METHODS OF MAKING DIAZAPEROPYRENIUM DICATIONS AND USES THEREOF

CROSS-REFERENCE TO RELATED APPLICATIONS

This application claims benefit of priority under 35 U.S.C. 119 to U.S. provisional patent application Ser. No. 61/883,352, filed Sep. 27, 2013, and entitled "METHODS OF MAKING DIAZAPEROPYRENIUM DICATIONS AND USES THEREOF," the content of which is herein incorporated by reference in its entirety.

STATEMENT OF GOVERNMENT INTEREST

This invention was made with government support under FA9550-07-1-0534 awarded by the Air Force Office for Scientific Research. The government has certain rights in the invention.

FIELD

The present disclosure relates to methods of making diazaperopyrenium dications.

BACKGROUND

Perylenes have been studied for over 140 years, but over 99% of perylenes researched are derivations of Perylene-3,4,9,10-tetracarboxylic acid diimides (PDI). More recent levels of sophistication include multifunctionalized perylene mono- and diimides sculpted into organic photovoltaic sensors, thin-film organic field effect transistors, nanofibers, (OFETs), and molecular electronics. Yet no robust synthetic processes exist in the art to enable production of diazaperopyrenium compounds with sensitive and versatile functional handles.

SUMMARY

In a first aspect, a method of making diazaperopyrenium dications is provided. The method includes providing 1,3,8,10-tetrahydro-2,9-diazadibenzo[cd,lm]perylene, said compound consists of formula (I):

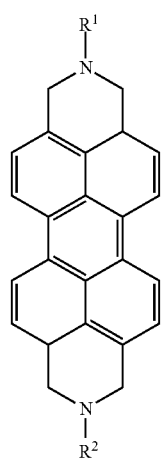

(I)

providing 2,3-dichloro-5,6-dicyano-1,4-benzoquinone (DDQ), and mixing said 1,3,8,10-tetrahydro-2,9-diazadibenzo[cd,lm]perylene with said DDQ to form a diazaperopyrenium dication, said diazaperopyrenium dication consists of formula (II):

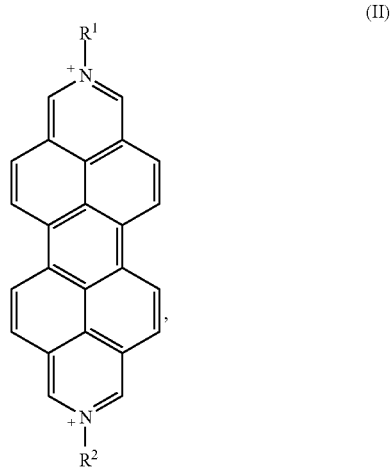

(II)

wherein the diazaperopyrenium dication of formula (II) is neutrally-balanced with counterion(s) $Q^-$.

In this aspect, $R^1$ and $R^2$ of diazaperopyrenium dication of formula (II) are each independently selected from a group consisting of structures (III)-(VII):

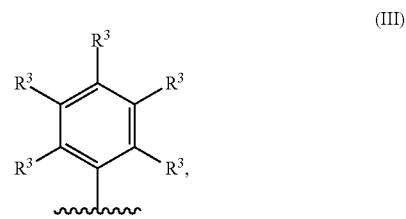

(III)

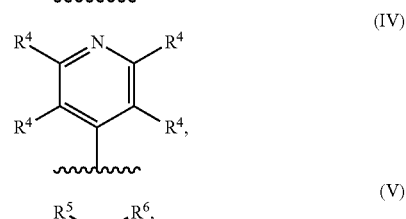

(IV)

(V)

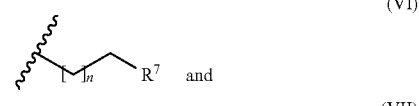

(VI)

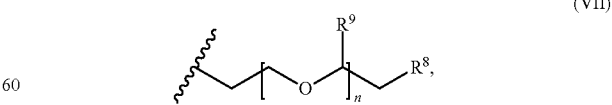

(VII)

wherein $R^3$, $R^4$, $R^5$, $R^6$, $R^7$ and $R^8$ are each independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone; $R^9$ is selected from hydrogen and methyl; and n is an integer in the range from 0 to 18.

In this aspect, counterions $Q^-$ are each independently selected from a group consisting of acetate, aceturate, acistrate, besylate, bromide, buciclate, butyrate, camsylate, caproate, citrate, chloride, closylate, cypionate, dapropate, edetate, edisylate, elaidate, enanthate, estolate, esylate, etabonate, etemesil, ethylesulfate, etzadroxil, formate, fostedate, fumarate, furoate, hemisuccinate, hybenzate, hydroxide, iodide, isethionate, lactate, laurate, maleate, mebutate, mesylate, napadisylate, napsylate, nitrite, oleate, oxalate, palmitate, pamoate, phosphate, perchlorate, phenproprionate, pivalate, proprionate, salicylate, sesquiolate, stearate, succinate, sulfate, tartate, thiocynate, tebutate, tosylate, triflate, trifluoroacetate, valerate, xinafoate, $BF_4$, and $PF_6$.

In a second aspect, a method of converting graphite to exfoliated graphene is provided. The method includes providing graphite, providing a diazaperopyrenium dication salt of formula (II):

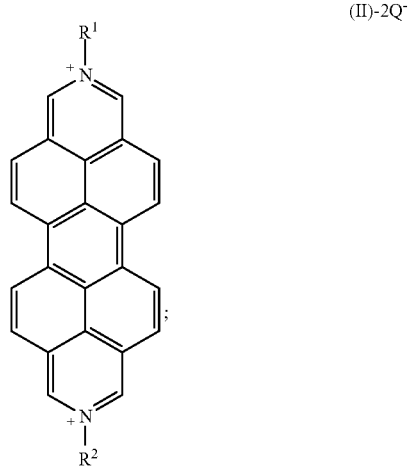

(II)-2Q$^-$ and mixing the graphite with the diazaperopyrenium dication salt to form exfoliated grapheme.

In this aspect, $R^1$ and $R^2$ of a diazaperopyrenium dication salt of formula (II) are each independently selected from a group consisting of structures (III)-(VII):

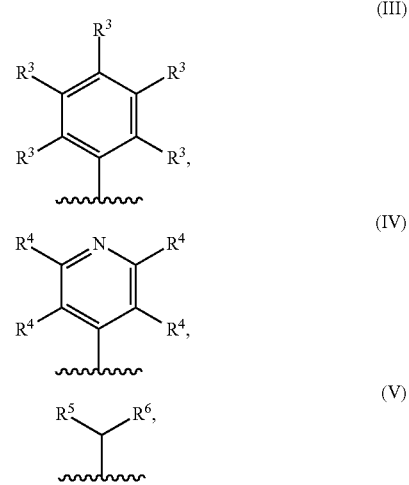

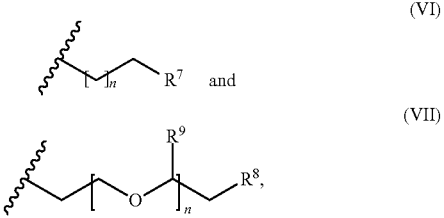

wherein $R^3$, $R^4$, $R^5$, $R^6$, $R^7$ and $R^8$ are each independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone; $R^9$ is selected from hydrogen and methyl; and n is an integer in the range from 0 to 18.

In this aspect, counterions $Q^-$ of a diazaperopyrenium dication salt of formula (II) are each independently selected from a group consisting of acetate, aceturate, acistrate, besylate, bromide, buciclate, butyrate, camsylate, caproate, citrate, chloride, closylate, cypionate, dapropate, edetate, edisylate, elaidate, enanthate, estolate, esylate, etabonate, etemesil, ethylesulfate, etzadroxil, formate, fostedate, fumarate, furoate, hemisuccinate, hybenzate, hydroxide, iodide, isethionate, lactate, laurate, maleate, mebutate, mesylate, napadisylate, napsylate, nitrite, oleate, oxalate, palmitate, pamoate, phosphate, perchlorate, phenproprionate, pivalate, proprionate, salicylate, sesquiolate, stearate, succinate, sulfate, tartate, thiocynate, tebutate, tosylate, triflate, trifluoroacetate, valerate, xinafoate, $BF_4$, and $PF_6$.

These and other features, objects and advantages of the present invention will become better understood from the description that follows. In the description, reference is made to the accompanying drawings, which form a part hereof and in which there is shown by way of illustration, not limitation, aspects of the invention.

Figure 1:
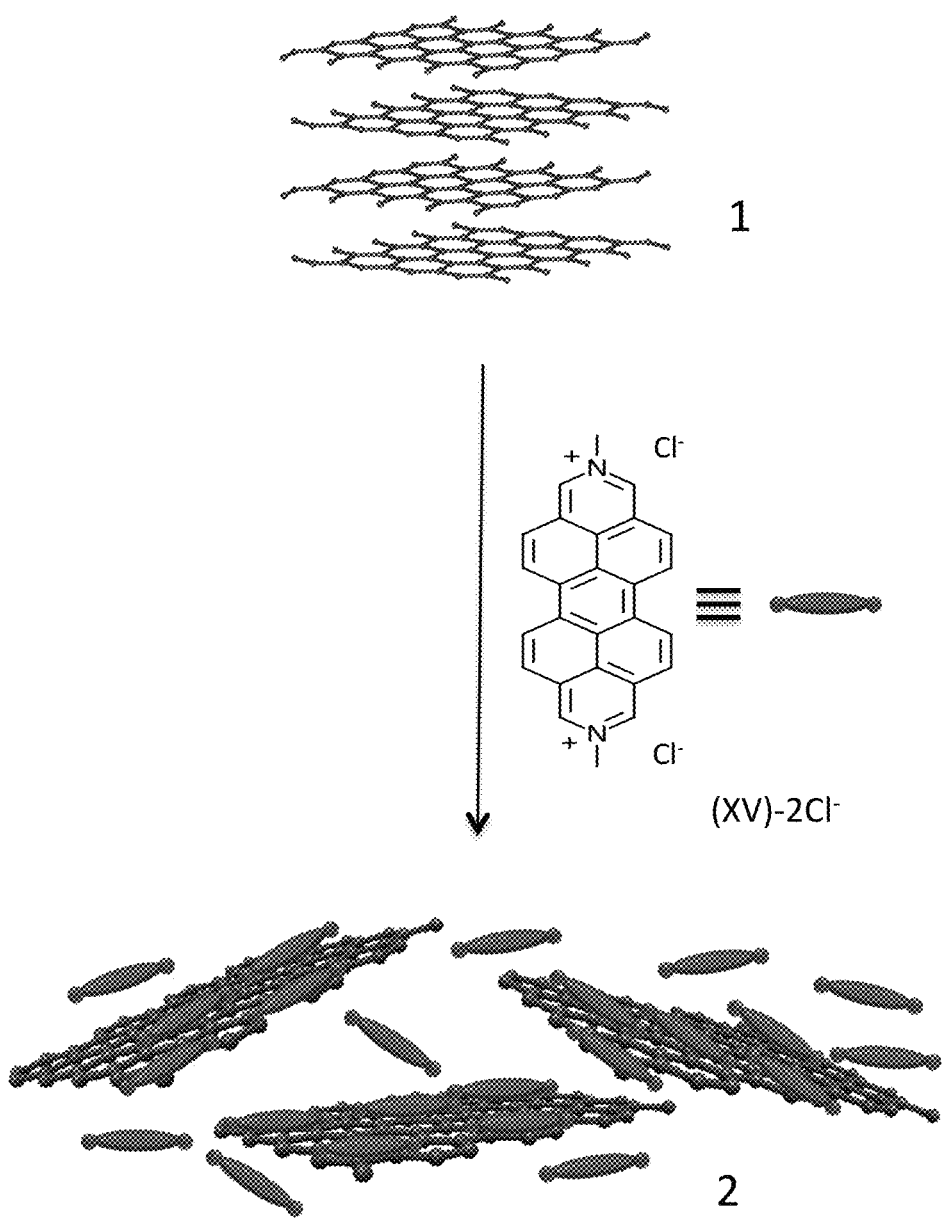
FIG. 1 depicts a reaction for the exfoliation of graphite (1) and stabilization of grapheme (2) in solvent by exposing graphite to a diazaperopyrenium dication salt ((XV)-2Cl$^-$).

While the present invention is amenable to various modifications and alternative forms, exemplary aspects thereof are shown by way of example in the drawings and are herein described in detail. It should be understood, however, that the description of exemplary aspects is not intended to limit the invention to the particular forms disclosed, but on the contrary, the intention is to cover all modifications, equivalents and alternatives falling within the spirit and scope of the invention as defined by the aspects above and the claims below. Reference should therefore be made to the aspects and claims herein for interpreting the scope of the invention.

DETAILED DESCRIPTION

The methods now will be described more fully hereinafter with reference to the accompanying drawings, in which some, but not all permutations and variations of aspects of the invention are shown. Indeed, the invention may be embodied in many different forms and should not be construed as limited to the aspects set forth herein. These aspects are provided in sufficient written detail to describe and enable one skilled in the art to make and use the invention, along with disclosure of the best mode for practicing the invention, as defined by the claims and equivalents thereof.

Likewise, many modifications and other aspects of the methods described herein will come to mind to one of skill in the art to which the invention pertains having the benefit of the teachings presented in the foregoing descriptions and the associated drawings. Therefore, it is to be understood that the invention is not to be limited to the specific aspects disclosed and that modifications and other aspects are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Certain terms are first defined. Additional terms are defined throughout the specification.

Terms used herein are intended as "open" terms (for example, the term "including" should be interpreted as "including but not limited to," the term "having" should be interpreted as "having at least," the term "includes" should be interpreted as "includes but is not limited to," etc.).

Furthermore, in those instances where a convention analogous to "at least one of A, B and C, etc." is used, in general such a construction is intended in the sense of one having ordinary skill in the art would understand the convention (for example, "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "from," "to," "up to," "at least," "greater than," "less than," and the like, include the number recited and refer to ranges which can subsequently be broken down into sub-ranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described aspects or features contained within the same. Where no options or choices are disclosed regarding a particular aspect or feature contained in the same, the modal verb "may" refers to an affirmative act regarding how to make or use and aspect of a described aspect or feature contained in the same, or a definitive decision to use a specific skill regarding a described aspect or feature contained in the same. In this latter context, the modal verb "may" has the same meaning and connotation as the auxiliary verb "can."

As used herein, the articles "a" and "an" refer to one or to more than one (for example, to at least one) of the grammatical object of the article.

"About" and "approximately" shall generally mean an acceptable degree of error for the quantity measured given the nature or precision of the measurements. Exemplary degrees of error are within 20-25 percent (%), typically, within 10%, and more typically, within 5% of a given value or range of values.

The chemical structures described herein are named according to IUPAC nomenclature rules and include art-accepted common names and abbreviations where appropriate. The IUPAC nomenclature can be derived with chemical structure drawing software programs, such as ChemDraw® (PerkinElmer, Inc.), ChemDoodle® (iChemLabs, LLC) and Marvin (ChemAxon Ltd.). The chemical structure controls in the disclosure to the extent that an IUPAC name is misnamed or otherwise conflicts with the chemical structure disclosed herein.

Headings, for example, (a), (b), (i) etc., are presented merely for ease of reading the specification and claims. The use of headings in the specification or claims does not require the steps or elements be performed in alphabetical or numerical order or the order in which they are presented.

The term "DDQ" refers to the chemical compound having the formula 2,3-dichloro-5,6-dicyano-1,4-benzoquinone, and represented by the following structure:

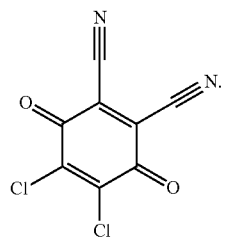 [SMILES: N#CC1=C(C#N)C(=O)C(Cl)=C(Cl)C1=O]

The present disclosure describes a novel method of making 2,9-diazaperopyrenium dications by aromatizing 1,3,8,10-tetrahydro-2,9-diazadibenzo[cd,lm]perylenes with 2,3-dichloro-5,6-dicyanodicyano-1,4-benzoquinone (DDQ). This method is economically advantageous over current methods of making 2,9-diazaperopyrenium dications. In addition, uses of 2,9-diazaperopyrenium dications are described. For example, the use of diazaperopyrenium dications to convert graphite to graphene is described. This method is unique over the well-known Hummer's method of creating graphene.

In a first aspect, a method of making 2,9-diazaperopyrenium dications by aromatizing 1,3,8,10-tetrahydro-2,9-diazadibenzo[cd,lm]perylene with 2,3-dichloro-5,6-dicyanodicyano-1,4-benzoquinone (DDQ) is described as shown in Scheme I.

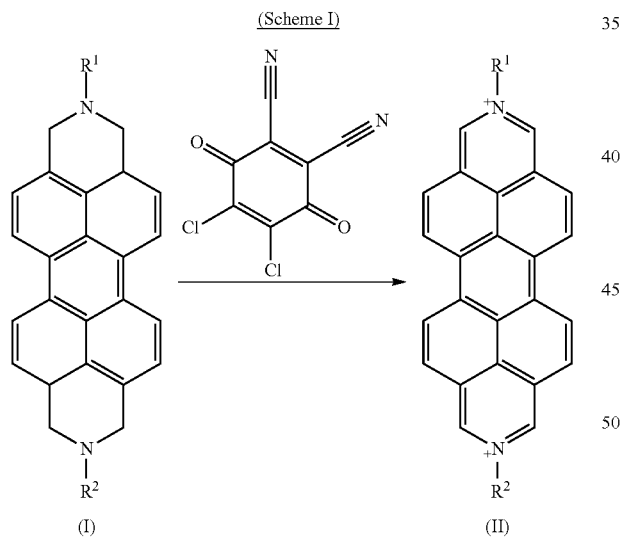

(Scheme I)

In this aspect, a 1,3,8,10-tetrahydro-2,9-diazadibenzo[cd,lm]perylene of structure (I) is provided. Then, 2,3-dichloro-5,6-dicyanodicyano-1,4-benzoquinone (DDQ) is provided. Next, the 2,9-perylene diimide is exposed to 2,3-dichloro-5,6-dicyano-1,4-benzoquinone (DDQ) to create a 2,9-diazaperopyrenium dication having structure (II). The 2,9-diazaperopyrenium dication can then be exposed to an ion exchange medium.

In this aspect, the 1,3,8,10-tetrahydro-2,9-diazadibenzo[cd,lm]perylene is provided corresponding to a compound of formula (I):

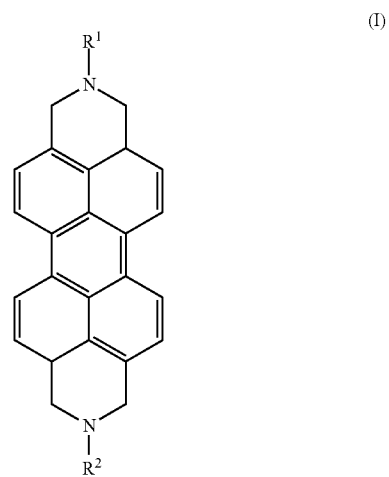

2,3-dichloro-5,6-dicyano-1,4-benzoquinone (DDQ) is provided, and 1,3,8,10-tetrahydro-2,9-diazadibenzo[cd,lm]perylene reacts with DDQ to form a diazaperopyrenium dication corresponding to a compound of formula (II):

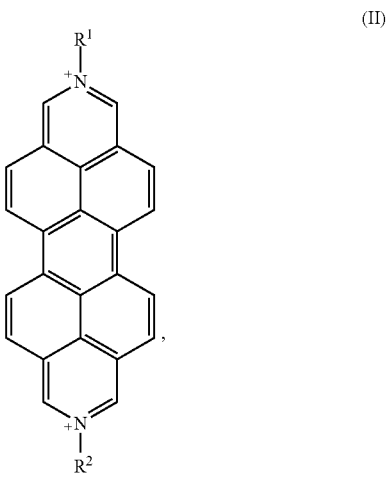

wherein the diazaperopyrenium dication of formula (II) is neutrally-balanced with counterion(s) Q$^-$.

In this aspect, $R^1$ and $R^2$ for compounds of formulas (I) and (II) are each independently selected from a group consisting of structures (III)-(VII):

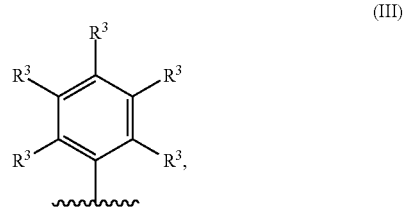

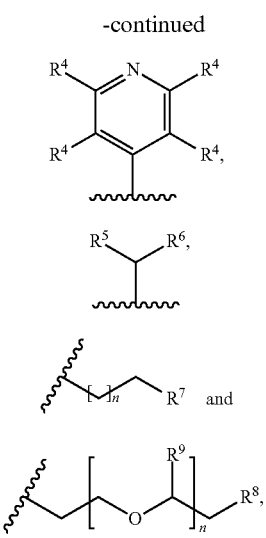

(IV)

(V)

(VI) and (VII)

wherein $R^3$, $R^4$, $R^5$, $R^6$, $R^7$ and $R^8$ are each independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone; $R^9$ is selected from hydrogen and methyl; and n is an integer in the range from 0 to 18.

The reactant 1,3,8,10-tetrahydro-2,9-diazadibenzo[cd,lm] perylene of formula (I) provided may be made by any method known to one of ordinary skill in the art. Exemplary examples of making 1,3,8,10-tetrahydro-2,9-diazadibenzo[cd,lm]perylene include Scheme 3 disclosed in "Self-Assembly of Cationic, Tetranuclear, Pt(II) and Pd(II) Macrocyclic Squares.X-ray Crystal Structure of [Pt²⁺(dppp)(4,4'-bipyridyl)2⁻OSO₂CF₃]₄" *J. Am. Chem. Soc.* 1995, 117, 6373-6283. In addition, the N-functionalization of the 1,3,8,10-tetrahydro-2,9-diazadibenzo[cd,lm]perylene need not be the same for specifying $R^1$ and $R^2$. For example, an exemplary method of making an asymmetric 2,9-perylene diimide is disclosed in"Self-Assembled Photoactive Polyelectrolyte/Perylene-Diimide Composites" *Langmuir* 2005, 21, 4149-4155. Another exemplary example of making an asymmetric 2,9-perylene diimide is disclosed in "Ultralong Nanobelts Self-Assembled from an Asymmetric Perylene Tetracarboxylic Diimide" *J. Am. Chem. Soc.* 2007, 23, 7234-7235. The asymmetric 1,3,8,10-tetrahydro-2,9-diazadibenzo[cd,lm]-perylene can then be prepared following procedure outlined in "Self-Assembly of Cationic, Tetranuclear, Pt(II) and Pd(II) Macrocyclic Squares.X-ray Crystal Structure of [Pt²⁺(dppp)(4,4'-bipyridyl)2⁻OSO₂CF₃]₄" *J. Am. Chem. Soc.* 1995, 117, 6373-6283 to prepare 1,3,8,10-tetrahydro-2,9-dimethyl-2,9-diazadibenzo[cd,lm]perylene.

Typical reaction conditions for Scheme I can include using polar aprotic solvent under atmospheric or neat $N_2$ conditions with a suitable reaction temperature. Examples of polar protic solvents include dichoromethane ($CH_2CCl_2$), tetrahydrofuran (cyc-$(CH_2)_4O$ or THF), ethyl acetate ($CH_3C(O)CH_2CH_3$), acetonitrile ($CH_3CN$ or MeCN), dimethylformamide ($HC(O)N(CH_3)_2$ or DMF), dimethyl sulfoxide (($CH_3)_2S(O)$ or DMSO), dimethyl ketone (($CH3)C(O)$ or acetone) and hexamethylphosphoric triamide ($[(CH_3)_2N]_3P(O)$ or HMPT), among others, including mixtures thereof. Suitable reaction temperatures can depend upon reactants, but exemplary reaction temperatures can range from ambient temperature to refluxing temperatures for the chosen solvent system.

In this aspect, the diazaperopyrenium dication of formula (II) from the reaction mixture from Scheme I can be subjected to ion exchange under suitable solvent or ion exchange chromatography conditions to provide suitable neutral-balanced salts with counterion(s) Q⁻. Counterion(s) Q⁻ are each independently selected from a group consisting of acetate, aceturate, acistrate, besylate, bromide, buciclate, butyrate, camsylate, caproate, citrate, chloride, closylate, cypionate, dapropate, edetate, edisylate, elaidate, enanthate, estolate, esylate, etabonate, etemesil, ethylesulfate, etzadroxil, formate, fostedate, fumarate, furoate, hemisuccinate, hybenzate, hydroxide, iodide, isethionate, lactate, laurate, maleate, mebutate, mesylate, napadisylate, napsylate, nitrite, oleate, oxalate, palmitate, pamoate, phosphate, perchlorate, phenproprionate, pivalate, proprionate, salicylate, sesquiolate, stearate, succinate, sulfate, tartate, thiocynate, tebutate, tosylate, triflate, trifluoroacetate, valerate, xinafoate, $BF_4$, and $PF_6$.

Exemplary compounds of diazaperopyrenium dication of formula (II) made according to Scheme I include compounds of formulas (VIII) to (XV):

(VIII)

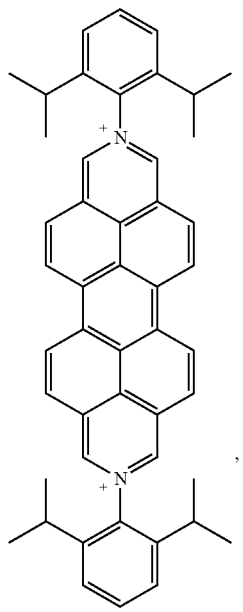

(IX)
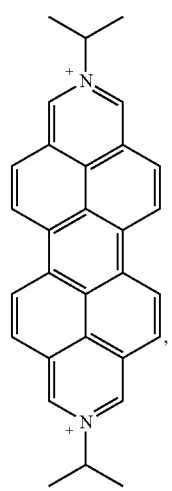
(XI)
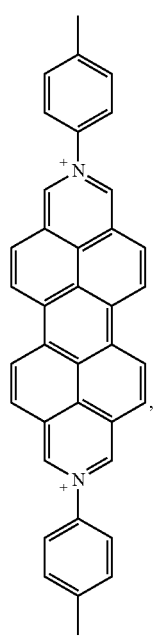
(X)
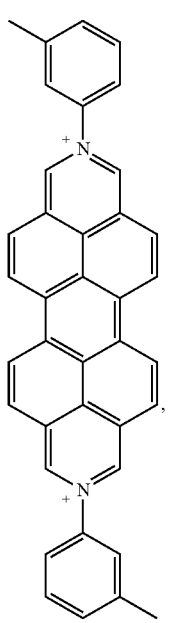
(XII)
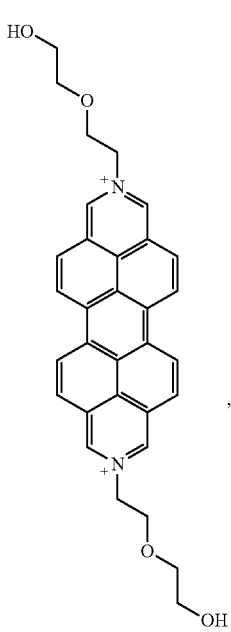

13
-continued

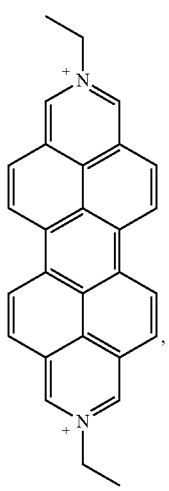
(XIII)

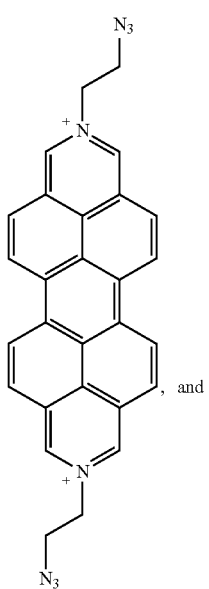
(XIV), and

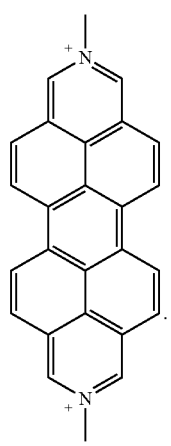
(XV).

Exemplary synthesis of these compounds is described in Examples 1-8.

14
Applications

The diazaperopyrenium dication of formula (II) and salts thereof have a variety of uses, including direct exfoliation of graphite to graphene in water at room temperature, uses in organic solar cells, organic field effect transistors (OFETs), organic dyes and fluorescent probes, photocatalysts for water splitting and $CO_2$ reduction, $I_2$-doped semiconductors, singlet oxygen generator, chemotherapeutic agents (for example, DNA intercalation and base-specific cleavage activities) and waste waster treatment.

Referring to FIG. 1, a method of converting graphite to exfoliated graphene is provided. The method includes providing graphite, providing a diazaperopyrenium dication salt of formula (II):

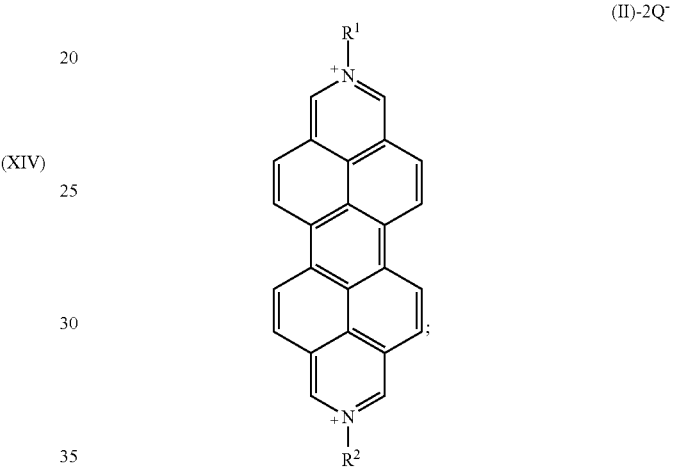
(II)-2Q⁻ and mixing the graphite with the diazaperopyrenium dication salt to form exfoliated graphene.

In this aspect, $R^1$ and $R^2$ of a diazaperopyrenium dication salt of formula (II) are each independently selected from a group consisting of structures (III)-(VII):

(III)

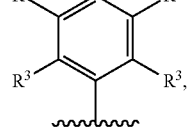
(IV)

(V)

(VI)

and

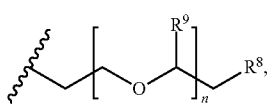

(VII)

wherein $R^3$, $R^4$, $R^5$, $R^6$, $R^7$ and $R^8$ are each independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone; $R^9$ is selected from hydrogen and methyl; and n is an integer in the range from 0 to 18.

In this aspect, counterions $Q^-$ of a diazaperopyrenium dication salt of formula (II) are each independently selected from a group consisting of acetate, aceturate, acistrate, besylate, bromide, buciclate, butyrate, camsylate, caproate, citrate, chloride, closylate, cypionate, dapropate, edetate, edisylate, elaidate, enanthate, estolate, esylate, etabonate, etemesil, ethylesulfate, etzadroxil, formate, fostedate, fumarate, furoate, hemisuccinate, hybenzate, hydroxide, iodide, isethionate, lactate, laurate, maleate, mebutate, mesylate, napadisylate, napsylate, nitrite, oleate, oxalate, palmitate, pamoate, phosphate, perchlorate, phenproprionate, pivalate, proprionate, salicylate, sesquiolate, stearate, succinate, sulfate, tartate, thiocynate, tebutate, tosylate, triflate, trifluoroacetate, valerate, xinafoate, $BF_4$, and $PF_6$.

Figure 2A:
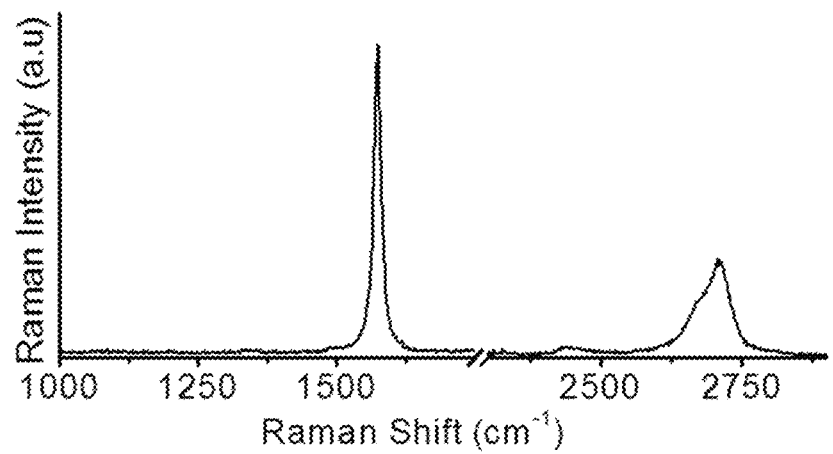
FIG. 2A depicts an exemplary Raman spectrum of graphite obtained by irradiating the sample with 514.5 nm wavelength light. Sample was prepared by drop-casting the solution on a silicon wafer and the solvent was removed under vacuum at room temperature.
Figure 2B:
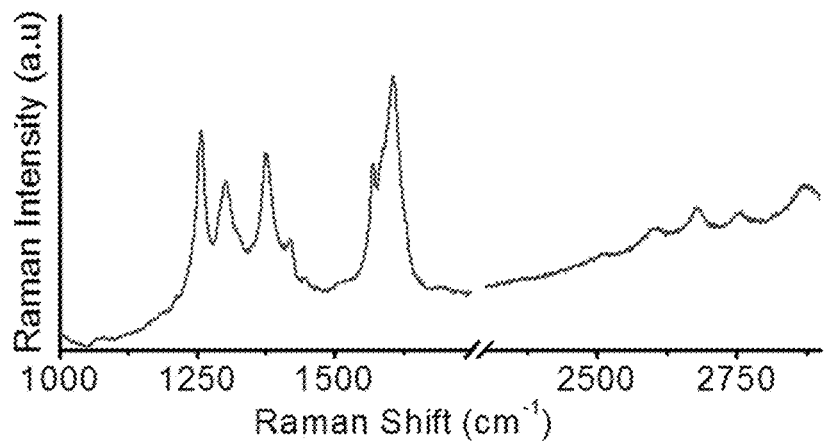
FIG. 2B depicts an exemplary Raman spectrum of diazaperopyrenium dication salt ((XV)-2Cl$^-$). Sample was prepared and irradiate as described in FIG. 2A.
Figure 2C:
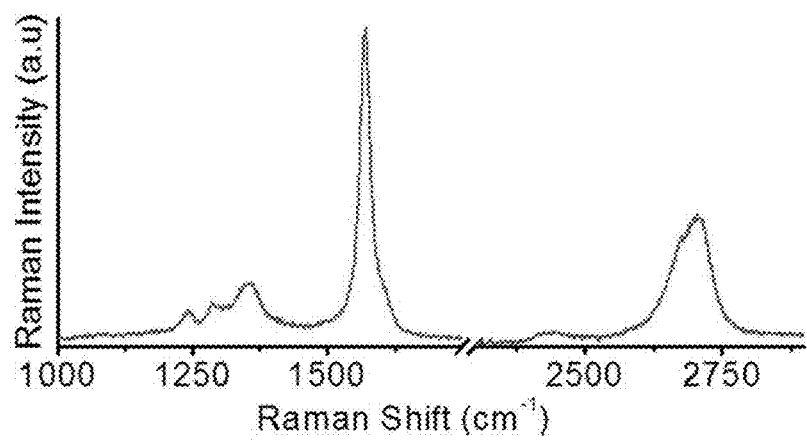
FIG. 2C depicts an exemplary Raman spectrum of graphene-diazaperopyrenium dication salt ((XV)-2Cl$^-$) composite material. Sample was prepared and irradiate as described in FIG. 2A.

FIG. 2 illustrates Raman spectroscopic analysis of graphite (FIG. 2A), diazaperopyrenium dication salt ((XV)-2Cl⁻) (FIG. 2B) and the graphene-diazaperopyrenium dication salt ((XV)-2Cl⁻) composite material (FIG. 2C). The Raman spectroscopy experiments were investigated for characteristic peaks to determine the quality of the exfoliated graphene. Graphite shows an intense G band peak at 1574 cm⁻¹ and a 2D band at 2708 cm⁻¹, while diazaperopyrenium dication salt ((XV)-2Cl⁻) shows Raman peaks at 1256, 1303 and 1375 cm⁻¹ corresponding to in-plane ring "breathing" (1420 cm⁻¹) indicative of ring deformation, and the peaks at 1569 and 1607 cm⁻¹ which are characteristic of in-plane C—C and C—N stretching modes. The graphene-diazaperopyrenium dication salt ((XV)-2Cl⁻) composite material shows an intense peak at 1571 cm⁻¹ (G band), small peaks at 1356 cm⁻¹ (D band), and another two weak bands at 1242 and 1287 cm¹ which could arise from diazaperopyrenium dication (XV) molecules present in the graphene composite. In addition to these signals, the composite mixture shows a strong 2D band peak at 2704 cm⁻¹ with an intensity ratio, $I_{2D}/I_G$, of 0.42, an increase compared to that of graphite ($I_{2D}/I_G$=0.31), further indicating that diazaperopyrenium dications ((XV)) exfoliate graphite to graphene. Moreover, the intense Raman peaks of diazaperopyrenium dication salt ((XV)-2Cl⁻) molecules were almost quenched in the composite as a consequence of π-π interactions between diazaperopyrenium dications ((XV)) and graphene.

Figure 3A:
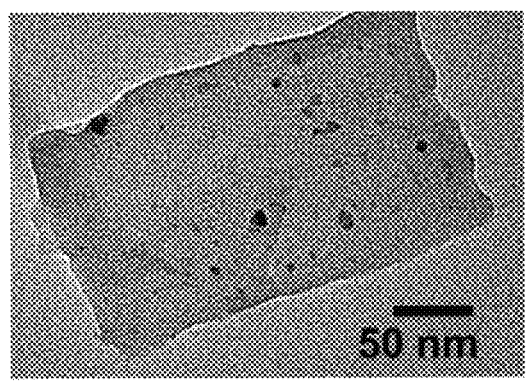
FIG. 3A depicts an exemplary transmission electron microscopy (TEM) image of graphene-diazaperopyrenium dication salt ((XV)-2Cl$^-$) composite material.
Figure 3B:
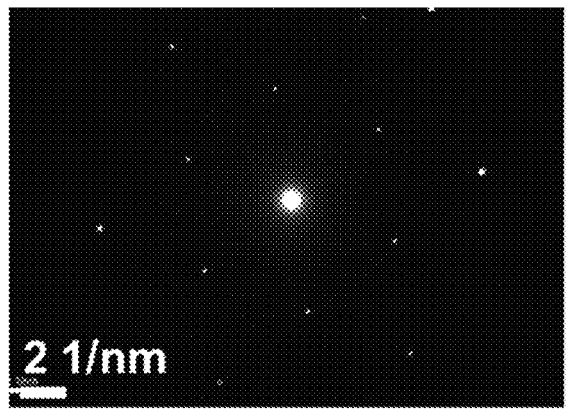
FIG. 3B depicts the Selected Area Electron Diffraction (SAED) pattern of graphene-diazaperopyrenium dication salt ((XV)-2Cl$^-$) composite material for TEM samples prepared by drop-casting the dilute composite dispersion on a carbon coated copper grid and solvent evaporated under vacuum at room temperature.
Figure 3C:
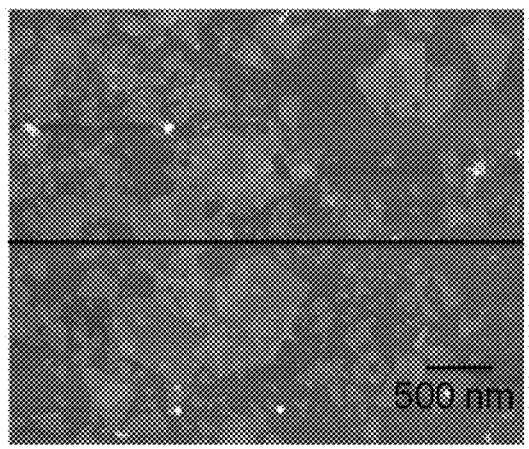
FIG. 3C depicts AFM height image of graphene-diazaperopyrenium dication salt ((XV)-2Cl⁻) composite material. AFM samples were prepared by spin-coating the dilute composite dispersion on a silicon wafer under ambient conditions.
Figure 3D:
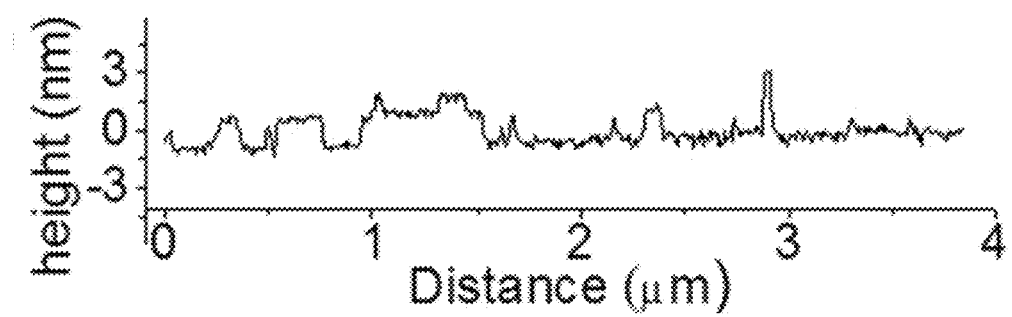
FIG. 3D depicts an exemplary height profile of AFM image corresponding to the line shown in FIG. 3C. AFM samples were prepared as described in FIG. 3B.
Figure 3E:
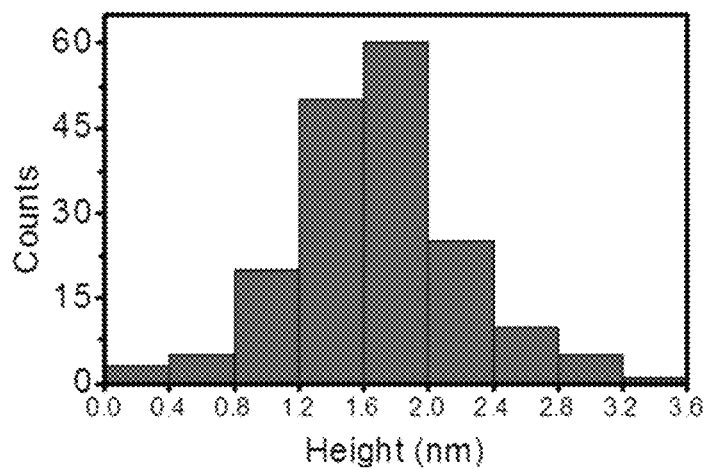
FIG. 3E depicts the probability of occurrence of graphene layers with various thickness calculated by measuring the thickness of the graphene sheets by AFM height image. AFM samples were prepared by spin-coating the dilute composite dispersion on a silicon wafer under ambient conditions. AFM samples were prepared as described in FIG. 3B.

Transmission electron microscopy (TEM) images (FIG. 3A) of diazaperopyrenium dication salt ((XV)-2Cl⁻)-graphene composite reveal the presence of graphene sheets in the diluted composite sample. A qualitative assessment of the thickness can be determined by Selected Area Electron Diffraction (SAED) measurements (FIG. 3B) on these graphene sheets. The expected six-fold symmetry and the presence of only a single set of spots indicate that these graphene sheets are single crystals and a majority are single or a few layers thick. The thicknesses of the graphene sheets were measured by atomic force microscopy (AFM), with both the AFM height image of graphene sheets (FIG. 3C), and the height profile of the AFM image (FIG. 3D) revealing the thickness of the graphene sheets, and the distribution of layer thickness (FIG. 3E). These observations reveal that the exfoliated graphene sheets are predominantly two to four layers thick.

Conductivity measurements give further insights into the applicability of this composite material as it relates to device settings. The conductivities of diazaperopyrenium dication salt ((XV)-2Cl⁻) and graphene-diazaperopyrenium dication salt ((XV)-2Cl⁻) composite material were measured in a parallel electrode, two-point probe configuration at room temperature (see Supporting Information). Both devices exhibited a linear I-V behavior, confirming Ohmic contact between the organic film and the electrodes. The conductivity of diazaperopyrenium dication salt ((XV)-2Cl⁻) was found to be $1.43 \times 10^{-3}$ S m⁻¹. Incorporation of graphene increases the conductivity by three orders of magnitude (3.57 S m⁻¹), indicating the formation of an interconnected conductive network within the composite material.

EXAMPLES

Example 1

Synthesis of the 2,9-bis(2,6-diisopropylphenyl)-diazaperopyrenium Hexafluorophosphate

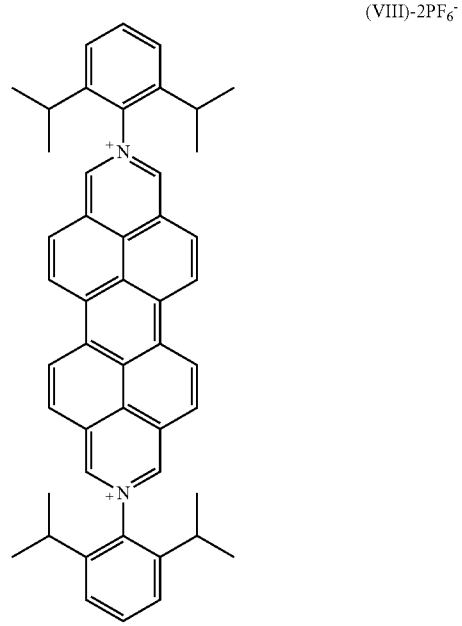

(VIII)-2PF₆⁻

3,4,9,10-tetra(chloromethyl)perylene (100 mg, 0.22 mmol) was added to neat 2,6-diisopropylaniline (20 mL) and the solution was stirred at 100° C. for 24 hrs under $N_2$. After cooling the solution to room temperature, $Et_2O$ (200 mL) was added to precipitate the crude product. The solution was filtered and the residue was washed with $Et_2O$ (3×20 mL) and dried to give a brown solid (115 mg, 78%). This crude material (91 mg, 0.14 mmol) was then added to MeCN (50 mL), followed by addition of DDQ (250 mg, 1.1 mmol) and this solution was then heated to reflux for 16 hrs. Upon cooling the solution to room temperature, 32% HCl solution (5 mL) and Et$_2$O (100 mL) were added to precipitate the chloride salt of the crude product. The solution was filtered and the residue was dissolved in a 50/50 mixture of (CH$_3$)$_2$CO/H$_2$O, to which excess NH$_4$PF$_6$ and H$_2$O were added to precipitate the PF$_6$ salt. The solution was filtered and the residue was washed with water (3×20 mL) and dried to give a brown/orange solid (80 mg, 61%). $^1$H NMR (CD$_3$CN, 500 MHz, 298 K): δ=10.06 (d, $^3$J=9.2 Hz, 4H), 9.93 (s, 4H), 9.03 (d, $^3$J=9.2 Hz, 4H), 7.83 (t, $^3$J=7.9 Hz, 2H), 7.65 (d, $^3$J=7.9 Hz, 4H), 2.12 (sep, $^3$J=6.7 Hz, 4H), 1.20 (d, $^3$J=6.7 Hz, 24H) ppm. $^{13}$C NMR (CD$_3$CN, 125 MHz, 298 K): δ=144.98, 140.45, 133.40, 131.36, 130.58, 130.34, 129.82, 128.07, 126.01, 122.94, 29.32, 24.20 ppm. ESI-MS: calcd for [M-2PF$_6$]$^{2+}$, m/z=325.1830. found: m/z=325.1839.

Example 2

Synthesis of the 2,9-diisopropyl-diazaperopyrenium Hexafluorophosphate

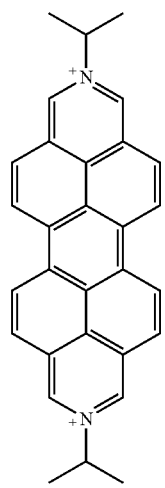

(IX)-2PF$_6^-$ 3,4,9,10-tetra(chloromethyl)perylene (100 mg, 0.22 mmol) was added to neat isopropylamine (20 mL) and the solution was stirred at room temperature for 24 hrs under N$_2$. Et$_2$O (200 mL) was added to precipitate the crude product. The solution was filtered and the residue was washed with Et$_2$O (3×20 mL) and dried to give a brown solid (71 mg, 75%). This crude material (60 mg, 0.14 mmol) was then added to MeCN (50 mL), followed by addition of DDQ (250 mg, 1.1 mmol) and this solution was then stirred at room temperature for 16 hrs. 32% HCl solution (5 mL) and Et$_2$O (100 mL) were added to precipitate the chloride salt of the crude product. The solution was filtered and the residue was dissolved in a 50/50 mixture of (CH$_3$)$_2$CO/H$_2$O, to which excess NH$_4$PF$_6$ and H$_2$O were added to precipitate the PF$_6$ salt. The solution was filtered and the residue was washed with water (3×20 mL) and dried to give a brown/orange solid (21 mg, 21%). $^1$H NMR (CD$_3$CN, 500 MHz, 298 K): δ=9.91 (s, 4H), 9.84 (d, $^3$J=9.2 Hz, 4H), 8.92 (d, $^3$J=9.2 Hz, 4H), 5.50 (sep, $^3$J=6.8 Hz, 2H), 1.98 (d, $^3$J=6.7 Hz, 12H) ppm. $^{13}$C NMR (CD$_3$CN, 125 MHz, 298 K): δ=137.77, 130.53, 129.82, 129.45, 129.39, 127.52, 122.59, 67.45, 23.77. ppm. ESI-MS: calcd for [M-PF$_6$]$^+$, m/z=559.1738. found: m/z=559.1742.

Example 3

Synthesis of the 2,9-bis(m-tolyl)-diazaperopyrenium Hexafluorophosphate

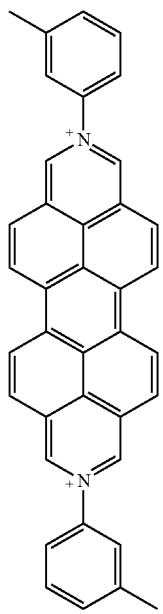

(X)-2PF$_6^-$ 3,4,9,10-tetra(chloromethyl)perylene (145 mg, 0.32 mmol) was added to neat m-toluidine (20 mL) and the solution was stirred at 60° C. for 24 hrs under N$_2$. After cooling the solution to room temperature, Et$_2$O (200 mL) was added to precipitate the crude product. The solution was filtered and the residue was washed with Et$_2$O (3×20 mL) and dried to give a brown solid (165 mg, quant.). This crude material (150 mg, 0.29 mmol) was then added to a MeCN/CH$_2$Cl$_2$ 50:50 mixture (50 mL), followed by addition of DDQ (250 mg, 1.1 mmol) and this solution was then heated to 60° C. for 16 hrs. Upon cooling the solution to room temperature, 32% HCl solution (5 mL) and Et$_2$O (100 mL) were added to precipitate the chloride salt of the crude product. The solution was filtered and the residue was dissolved in a 50/50 mixture of (CH$_3$)$_2$CO/H$_2$O, to which excess NH$_4$PF$_6$ and H$_2$O were added to precipitate the PF$_6$ salt. The solution was filtered and the residue was washed with water (3×20 mL) and dried to give a brown/orange solid (23 mg, 10%). $^1$H NMR (CD$_3$CN, 500 MHz, 298 K): δ=10.09 (s, 4H), 9.89 (d, $^3$J=9.3 Hz, 4H), 8.99 (d, $^3$J=9.3 Hz, 4H), 7.93 (s, 2H), 7.89 (d, $^3$J=7.8 Hz, 2H), 7.79 (t, $^3$J=7.8 Hz, 4H), 7.73 (d, $^3$J=7.8 Hz, 2H), 2.63 (s, 6H) ppm. $^{13}$C NMR (CD$_3$CN, 125 MHz, 298 K): δ=144.62, 142.48, 139.44, 133.31, 131.52, 130.38, 130.24, 129.97, 129.30, 127.73, 126.63, 123.19, 122.72, 21.40. ppm. ESI-MS: calcd for [M-2PF$_6$]$^{2+}$, m/z=255.1048. found: m/z=255.1053.

Example 4

Synthesis of the 2,9-bis(p-tolyl)-diazaperopyrenium Hexafluorophosphate

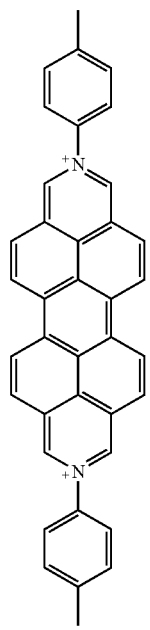

(XI)-2PF$_6^-$ 3,4,9,10-tetra(chloromethyl)perylene (100 mg, 0.22 mmol) was added to anhydrous THF (20 mL), followed by addition of p-toluidine (4.8 g) and the solution was stirred at 60° C. for 16 hrs under $N_2$. After cooling the solution to room temperature, $Et_2O$ (200 mL) was added to precipitate the crude product. The solution was filtered and the residue was washed with $Et_2O$ (3×20 mL) and dried to give a brown solid (110 mg, 95%). This crude material (100 mg, 0.19 mmol) was then added to a MeCN/$CH_2Cl_2$ 50:50 mixture (50 mL), followed by addition of DDQ (530 mg, 2.3 mmol) and this solution was then heated to 40° C. for 3 days. Upon cooling the solution to room temperature, 32% HCl solution (5 mL) and $Et_2O$ (100 mL) were added to precipitate the chloride salt of the crude product. The solution was filtered and the residue was dissolved in a 50/50 mixture of $(CH_3)_2CO/H_2O$, to which excess $NH_4PF_6$ and $H_2O$ were added to precipitate the $PF_6$ salt. The solution was filtered and the residue was washed with water (3×20 mL) and dried to give a brown/orange solid (20 mg, 13%). $^1$H NMR (CD$_3$CN, 500 MHz, 298 K): δ=10.07 (s, 4H), 9.78 (d, $^3J$=9.3 Hz, 4H), 8.94 (d, $^3J$=9.3 Hz, 4H), 7.97 (d, $^3J$=8.4 Hz, 4H), 7.73 (d, $^3J$=8.4 Hz, 4H), 2.61 (s, 6H) ppm. $^{13}$C NMR (CD$_3$CN, 125 MHz, 298 K): δ=143.64, 142.34, 139.42, 132.19, 130.17, 130.06, 129.82, 129.24, 127.68, 125.91, 122.55, 21.26. ppm. ESI-MS: calcd for [M-2PF$_6$]$^{2+}$, m/z=255.1048. found: m/z=255.1051.

Example 5

Synthesis of the 2,9-bis(2-(2-hydroxyethoxy)ethyl)-diazaperopyrenium Hexafluorophosphate

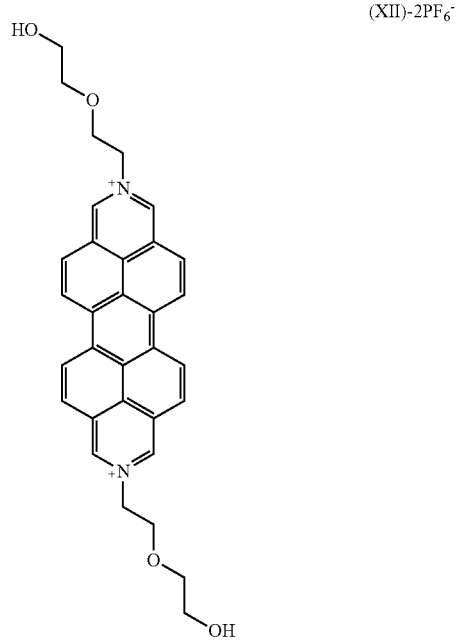

(XII)-2PF$_6^-$ 1,3,8,10-Tetrahydro-2,9-diethylene glycol-diazadibenzo[cd,lm]perylene (2.5 g, 4.4 mmol) was added to anhydrous THF (200 mL), followed by slow addition of BH$_3$-DMS (2M in THF, 50 mL) and the solution was stirred at reflux for 5 days under $N_2$. After cooling the solution to room temperature, the solution was quenched by the slow addition of MeOH (200 mL). HCl solution (6M, 100 mL) was added and the solution was stirred at reflux for 3 hours. Upon cooling the solution to room temperature, the solvent was removed under vacuum and the residue was suspended in a saturated potassium carbonate solution until the pH reached 10. The suspension was then filtered and the residue was washed with water (3 x×50 mL) and dried to give a brown solid (1.4 g, 62%). This crude material (1.2 g, 2.4 mmol) was then added to a MeCN/CH$_2$Cl$_2$ 50:50 mixture (200 mL), followed by addition of DDQ (4.4 g mg, 19.4 mmol) and this solution was then stirred at RT for 3 days. HCl solution (32%, 5 mL) and Et$_2$O (100 mL) were added to precipitate the chloride salt of the crude product. The solution was filtered and the residue was dissolved in H$_2$O (50 mL), to which excess NH$_4$PF$_6$ was added to precipitate the PF$_6$ salt. The solution was filtered and the residue was washed with water (3×20 mL) and dried to give a brown/orange solid (0.47 g, 25%). $^1$H NMR (CD$_3$CN, 500 MHz, 298 K): δ=9.72 (s, 4H), 8.41 (br s, 4H), 8.18 (d, $^3J$=9.0 Hz, 4H), 5.31 (t, $^3J$=4.8 Hz, 4H), 4.35 (t, $^3J$=4.8 Hz, 4H), 3.78 (s, 8H) ppm. $^{13}$C NMR (CD$_3$CN, 125 MHz, 298 K): δ=140.06, 128.94, 128.07, 127.90, 127.79, 127.02, 120.59, 73.56, 69.88, 63.57, 61.83. ppm. ESI-MS: calcd for [M-PF$_6$]$^+$, m/z=651.1847. found: m/z=651.1848.

Example 6

Synthesis of the 2,9-diethyl-diazaperopyrenium Hexafluorophosphate

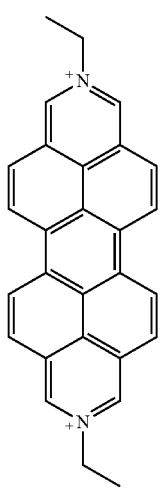

(XIII)-2PF$_6^-$ 3,4,9,10-tetra(chloromethyl)perylene (100 mg, 0.22 mmol) was added to neat ethylamine (20 mL) and the solution was stirred at room temperature for 24 hrs under $N_2$. Et$_2$O (200 mL) was added to precipitate the crude product. The solution was filtered and the residue was washed with Et$_2$O (3×20 mL) and dried to give a dark red solid (69 mg, 74%). This crude material (69 mg, 0.17 mmol) was then added to MeCN (50 mL), followed by addition of DDQ (372 mg, 1.4 mmol) and this solution was then stirred at reflux under an O$_2$ atmosphere for 16 hrs, then cooled to room temperature. 37% HCl solution (5 mL) was added to precipitate the chloride salt of the crude product. The solution was filtered and the residue was dissolved in a 50/50 mixture of (CH$_3$)$_2$CO/H$_2$O, to which excess NH$_4$PF$_6$ and H$_2$O were added to precipitate the PF$_6$ salt. The solution was filtered and the residue was washed with water (3×20 mL) and dried to give a red solid (108 mg, 88%). LCQ ESI-MS: calcd for [M-PF$_6$]$^+$, m/z=676.43. found: m/z=676.4.

Example 7

Synthesis of the 2,9-bis(2-azidoethyl)-diazaperopyrenium Dication with Alternate Conditions

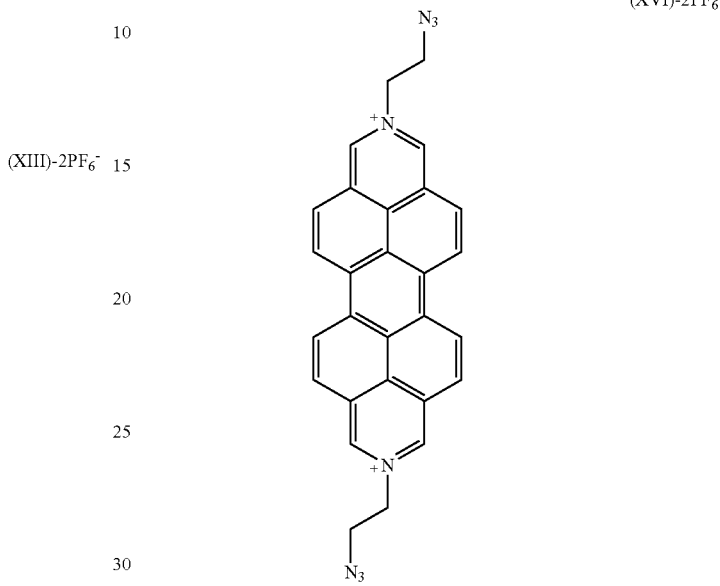

(XVI)-2PF$_6^-$ 3,4,9,10-tetra(chloromethyl)perylene (130 mg, 58.1 mmol) was added to 2-azidoethanamine (4.99 g, 290 mmol) dissolved in CH$_2$Cl$_2$ (20 mL) and the reaction mixture was stirred vigorously at 23° C. for 48 h. The solvent was removed by evaporation under reduced pressure and the residue was suspended in H$_2$O, filtered and washed with H$_2$O (2×50 mL) and Et$_2$O (2×50 mL) to afford a pure sample of the diazide (102 mg, 74%) as a reddish-brown powder. The diazide (119 mg, 0.252 mmol) was suspended in anhydrous THF (25 mL). DDQ (458 mg, 2.02 mmol) was added slowly, and the reaction mixture was heated to 50° C. under an O$_2$ atmosphere for 16 h before being cooled to 23° C. A solution of 37% HCl (3 mL) was pipetted into the mixture, whereupon precipitation occurred. The precipitate was filtered and washed with MeCN (3×25 mL) and Et$_2$O (3×25 mL) to afford (66 mg, 57%) the dark red dichloride salt. Counterion exchange was performed by dissolving the salt in 1:1 Me$_2$CO/H$_2$O, adding excess of NH$_4$PF6, and evaporating of the Me$_2$CO. The resulting precipitate was filtered and washed with excess of H$_2$O to afford the crude product. Recrystallization from Me$_2$CO and Et$_2$O afforded (44 mg, 25% yield) the product as a red solid. $^1$H NMR (500 MHz, (CD$_3$)$_2$CO$_3$ 25° C.): δ (ppm)=10.43 (s, 4H, H$_a$), 10.21 (d, J=9 Hz, 4H, H$_d$), 9.17 (d, J=9 Hz, 4H, H$_g$), 5.64 (t, J=5 Hz, 4H, Ha), 4.58 (t, J=5 Hz, 4H, H$_b$) ppm (FIG. 2.10). $^{13}$C NMR (125 MHz, CD$_3$CN, 25° C.): δ (ppm)=139.0, 128.1, 126.4, 61.5, 53.6. HRMS (ESI) calcd for C$_{28}$H$_{20}$F$_6$N$_8$P m/z=613.1453 [M]$^+$. found m/z=613.1447 [M]$^+$.

Example 8

Synthesis of the 2,9-dimethyl-diazaperopyrenium Hexafluorophosphate

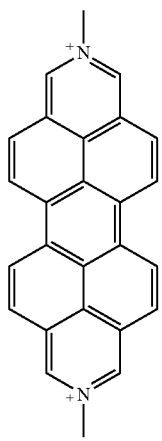

(XV)-2PF$_6^-$ 1,3,8,10-Tetrahydro-2,9-dimethyl-2,9-diazadibenzo[cd,lm]-perylene (100 mg, 274 mmol) was suspended at 23° C. in anhydrous MeCN (10 mL). 2,3-Dichloro-5,6-dicyano-1,4-benzoquinone (DDQ; 249 mg, 1.10 mmol) was added as a solid, thereby resulting in an immediate color change from green to dark brown. The reaction mixture was heated under reflux for 16 h, before being cooled to 25° C. A solution of 37% HCl (3 mL) was pipetted into the flask, whereupon precipitation occurred. The precipitate was filtered off and washed with MeCN (3×25 mL) and Et$_2$O (3×25 mL) to afford the dark green dichloride salt product (100 mg). Counterion exchange was performed by dissolving the dichloride salt in MeOH/H$_2$O (1:1) mixture, adding an excess of NH$_4$PF$_6$, and removing the MeOH using rotary evaporation. The resulting precipitate was filtered and washed with an excess of H$_2$O to afford the final (XV)-2PF$_6^-$ salt product (136 mg, 77%). $^1$H NMR (500 MHz, (CD$_3$)$_2$CO, 258C): d=10.21 (s, 4H), 9.99 (d, J=9 Hz, 4H), 9.00 (d, J=9 Hz, 4H), 5.11 ppm (s, 6. $^{13}$C NMR (125 MHz, CD$_3$CN, 25 8° C.): d=139.1, 128.6, 128.3, 127.8, 126.0, 121.4, 49.0 ppm. HRMS (ESI) calcd for C$_{26}$H$_{18}$F$_6$N$_2$P: m/z=503.1106 [M]$^+$. found: m/z=503.1106 [M]$^+$.

Example 9

Creation of Graphene from Graphite by Exposure to a Diazaperopyrenium Dication Graphite powder (synthetic, conducting grade, 325 mess, 99.9995%, metals basis) was obtained from Alfa Aesar. N,N'-dimethyl-2,9-diazaperopyrenium dication hexafluorophosphate was synthesized as described in Example 8 and converted to Cl$^-$ salts using tetrabutylammonium chloride (n-Bu$_4$NCl). All of the other reagents and solvents were purchased from commercial sources and were used without further purification, unless indicated otherwise. Raman spectra were recorded using a confocal Raman spectroscope 2018 model gas laser and an excitation wavelength of 514.5 nm. X-Ray photoelectron spectroscopy (XPS) measurements were conducted on a Thermo XPS ESCALAB 250Xi instrument with an Al K α (1486.8 eV) X-ray source and samples were measured under an ultrahigh vacuum (<10$^{-9}$ mbar). Ultraviolet photoelectron spectroscopy (UPS) measurements were conducted on a Thermo XPS ESCALAB 250Xi instrument with an HeI (21.2 eV) ultraviolet source and samples were measured under an ultrahigh vacuum (2×10$^{-8}$ mbar). All binding energies were calibrated using the C(1s) carbon peak (284.6 eV). TEM studies were conducted using a TEM-JEOL-2100F at an accelerating electron voltage of 200 kV. AFM images were measured using an AFMICON instrument under ambient conditions.

REFERENCES

Basuray, A. N., Jacquot de Rouville, H.-P., Hartlieb, K. J., Fahrenbach, A. C., Stoddart, J. F. "Beyond Perylene Diimides—Diazaperopyrenium Dications as Chameleonic Nanoscale Building Blocks," *Chem. Asian. J.* 2012, DOI: 10.1002/asia.201200780.

Basuray, A. N, Jacquot de Rouville, H.-P., Hartlieb, K. J., Kikuchi, T., Strutt, N. L., Bruns, C. J., Ambrogio, M. W., Avestro, A.-J., Schneebeli, S. T., Fahrenbach, A. C., Stoddart, J. F. "The Chameleonic Nature of Diazaperopyrenium Recognition Processes," *Angew. Chem. Int. Ed.* 2012, 51, 11872-11877.

Sampath, S., Basuray, A. N., Hartlieb, K. J., Aytun, T., Stupp, S. I., Stoddart, J. F. "Direct Exfoliation of Graphite to Graphene in Aqueous Media with Diazaperopyrenium Dications," *Adv. Mater.* 2013. DOI: 10.1002/adma.201205157.

Hartlieb, K. J., Basuray, A. N., Ke, C., Sarjeant, A. A., Jacquot de Rouville, H.-P., Kikuchi, T., Forgan, R. S., Kurutz, J. W., Stoddart. J. F. "Chameleonic binding of the dimethyldiazaperopyrenium dication by cucurbit[8]uril," *Asian J. Org. Chem.* 2013, 2, 225-229.

All of the patents, patent applications, patent application publications and other publications recited herein are hereby incorporated by reference as if set forth in their entirety.

The present invention has been described in connection with what are presently considered to be the most practical and preferred aspects. However, the invention has been presented by way of illustration and is not intended to be limited to the disclosed aspects. Accordingly, one of skill in the art will realize that the invention is intended to encompass all modifications and alternative arrangements within the spirit and scope of the invention as set forth in the appended claims.

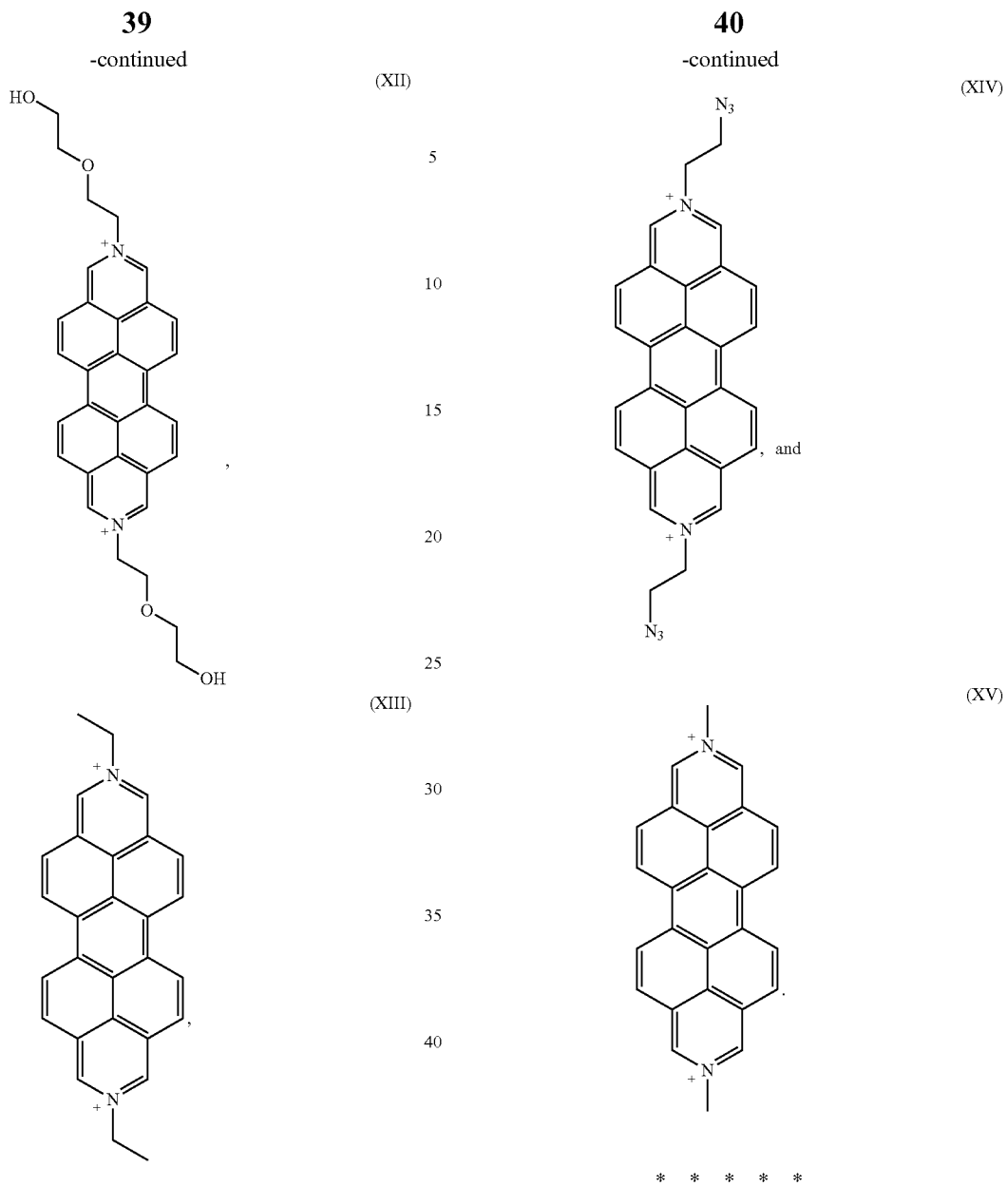

What is claimed is:

1. A method of making a diazaperopyrenium dication, comprising:
   providing 1,3,8,10-tetrahydro-2,9-diazadibenzo[cd,lm] perylene of formula (I):

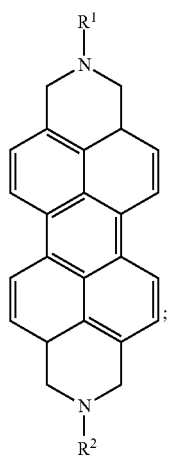 (I)

providing 2,3-dichloro-5,6-dicyano-1,4-benzoquinone; and reacting 1,3,8,10-tetrahydro-2,9-diazadibenzo[cd,lm]perylene of formula (I) with 2,3-dichloro-5,6-dicyano-1,4-benzoquinone to form a diazaperopyrenium dication of formula (II):

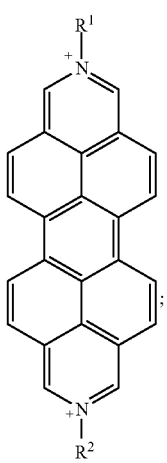 (II)

wherein the diazaperopyrenium dication of formula (II) is neutrally-balanced with counterion(s) $Q^-$, $R^1$ and $R^2$ of formulas (I) and (II) are each independently selected from a group consisting of structures (III)-(VII):

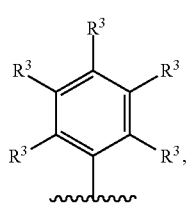 (III)

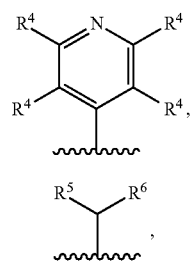 (IV)

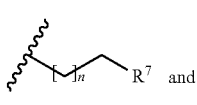 (V)

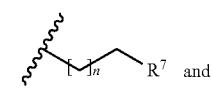 (VI)

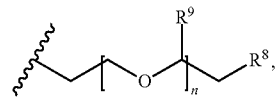 (VII)

$R^3$, $R^4$, $R^5$, $R^6$, $R^7$ and $R^8$ are each independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone;

$R^9$ is selected from hydrogen and methyl;

n is an integer in the range from 0 to 18; and counterion(s) $Q^-$ is selected from a group consisting of acetate, aceturate, acistrate, besylate, bromide, buciclate, butyrate, camsylate, caproate, citrate, chloride, closylate, cypionate, dapropate, edetate, edisylate, elaidate, enanthate, estolate, esylate, etabonate, etemesil, ethylesulfate, etzadroxil, formate, fostedate, fumarate, furoate, hemisuccinate, hybenzate, hydroxide, iodide, isethionate, lactate, laurate, maleate, mebutate, mesylate, napadisylate, napsylate, nitrite, oleate, oxalate, palmitate, pamoate, phosphate, perchlorate, phenproprionate, pivalate, proprionate, salicylate, sesquiolate, stearate, succinate, sulfate, tartate, thiocynate, tebutate, tosylate, triflate, trifluoroacetate, valerate, xinafoate, $BF_4$, and $PF_6$.

2. The method of claim 1, wherein $R^1$ and $R^2$ of formulas (I) and (II) are identical substituents selected from a group consisting of structures (III)-(VII):

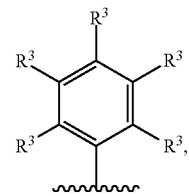 (III)

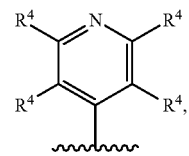 (IV)

-continued

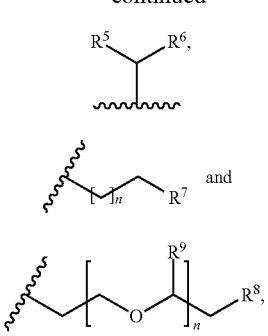

wherein $R^3$, $R^4$, $R^5$, $R^6$, $R^7$ and $R^8$ are each independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone;

$R^9$ is selected from hydrogen and methyl; and n is an integer in the range from 0 to 18.

3. The method of claim 2, wherein $R^3$, $R^4$, $R^5$, $R^6$, $R^7$ and $R^8$ are each independently selected from a group consisting of hydrogen, halogen, $C_{1-18}$ alkyl, $C_{3-8}$ cycloalkyl, $C_{5-20}$ aryl, alcohol, ester, anhydride, amine and azide.

4. The method of claim 3, wherein $R^3$, $R^4$, $R^5$, $R^6$, $R^7$ and $R^8$ are each independently selected is selected from a group consisting of hydrogen, chlorine, bromine, fluorine, iodine, methyl, ethyl, isopropyl, hydroxyl, amine and azide.

5. The method of claim 1, wherein $R^1$ and $R^2$ of formulas (I) and (II) consist of structure (III):

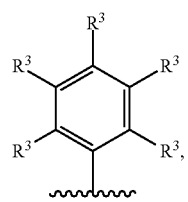

wherein $R^3$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone.

6. The method of claim 1, wherein $R^1$ and $R^2$ of formulas (I) and (II) consist of structure (IV):

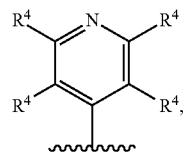

wherein $R^4$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone.

7. The method of claim 1, wherein $R^1$ and $R^2$ of formulas (I) and (II) consist of structure (V):

wherein $R^5$ and $R^6$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone.

8. The method of claim 1, wherein $R^1$ and $R^2$ of formulas (I) and (II) consist of structure (VI):

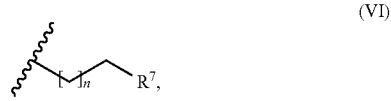

wherein $R^7$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone; and n is an integer in the range from 0 to 18.

9. The method of claim 1, wherein $R^1$ and $R^2$ of formulas (I) and (II) consist of structure (VII):

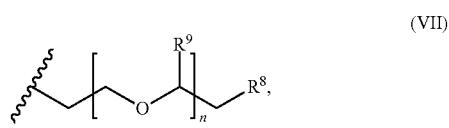

wherein $R^8$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone;

$R^9$ is selected from hydrogen and methyl; and n is an integer in the range from 0 to 18.

10. The method of claim 1, wherein the diazaperopyrenium dication of formula (II) is selected from a group consisting of formulas (VIII) to (XV):

(VIII)
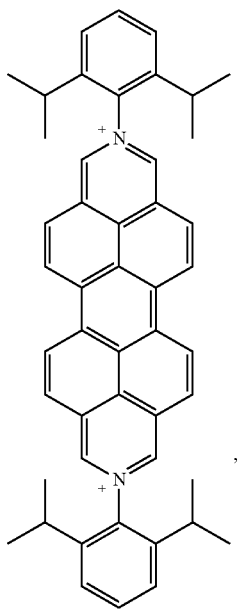
(X)
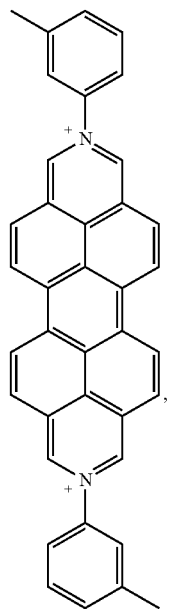
(IX)
(XI)
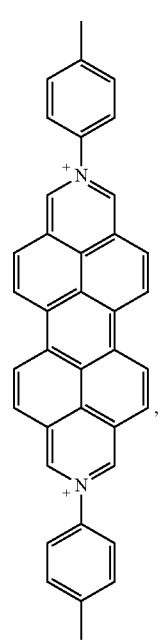

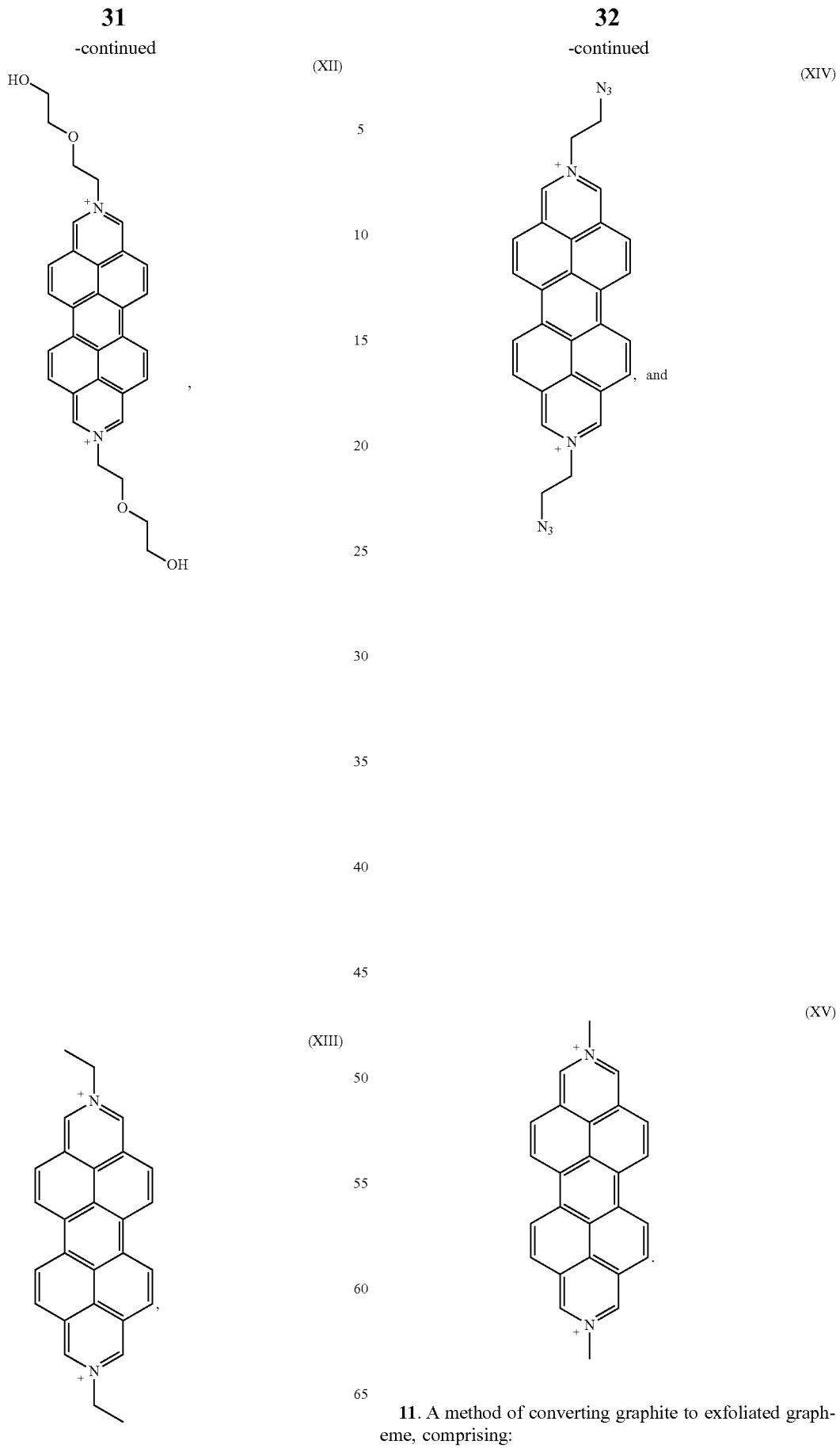
11. A method of converting graphite to exfoliated grapheme, comprising:

providing graphite;
providing a diazaperopyrenium dication of formula (II):

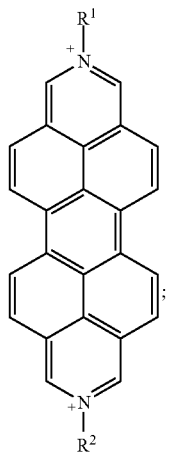

and
mixing graphite with the diazaperopyrenium dication of formula (II) to form exfoliated grapheme,
wherein the diazaperopyrenium dication is neutrally-balanced with counterion(s) $Q^-$,
$R^1$ and $R^2$ of formula (II) are each independently selected from a group consisting of structures (III)-(VII):

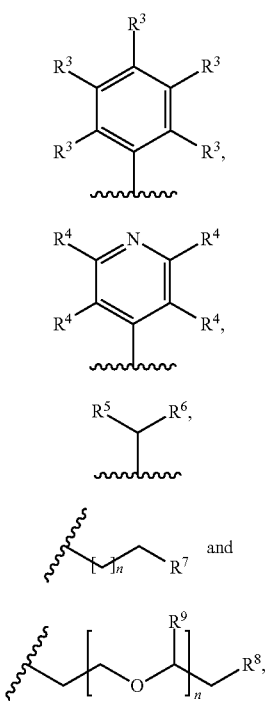

$R^3$, $R^4$, $R^5$, $R^6$, $R^7$ and $R^8$ are each independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone;

$R^9$ is selected from hydrogen and methyl;
n is an integer in the range from 0 to 18; and
counterion(s) $Q^-$ is selected from a group consisting of acetate, aceturate, acistrate, besylate, bromide, buciclate, butyrate, camsylate, caproate, citrate, chloride, closylate, cypionate, dapropate, edetate, edisylate, elaidate, enanthate, estolate, esylate, etabonate, etemesil, ethylesulfate, etzadroxil, formate, fostedate, fumarate, furoate, hemisuccinate, hybenzate, hydroxide, iodide, isethionate, lactate, laurate, maleate, mebutate, mesylate, napadisylate, napsylate, nitrite, oleate, oxalate, palmitate, pamoate, phosphate, perchlorate, phenproprionate, pivalate, proprionate, salicylate, sesquiolate, stearate, succinate, sulfate, tartate, thiocynate, tebutate, tosylate, triflate, trifluoroacetate, valerate, xinafoate, $BF_4$, and $PF_6$.

12. The method of claim 11, wherein $R^1$ and $R^2$ of formula (II) are identical substituents selected from a group consisting of structures (III)-(VII):

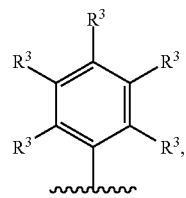

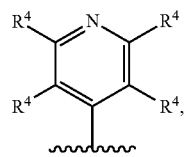

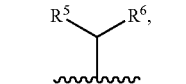

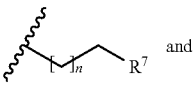

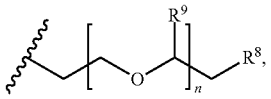

wherein $R^3$, $R^4$, $R^5$, $R^6$, $R^7$ and $R^8$ are each independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone;

$R^9$ is selected from hydrogen and methyl; and
n is an integer in the range from 0 to 18.

13. The method of claim 12, wherein $R^3$, $R^4$, $R^5$, $R^6$, $R^7$ and $R^8$ are each independently selected from a group consisting of hydrogen, halogen, $C_{1-18}$ alkyl, $C_{3-8}$ cycloalkyl, $C_{5-20}$ aryl, alcohol, ester, anhydride, amine and azide.

14. The method of claim 13, wherein $R^3$, $R^4$, $R^5$, $R^6$, $R^7$ and $R^8$ are each independently selected is selected from a group consisting of hydrogen, chlorine, bromine, fluorine, iodine, methyl, ethyl, isopropyl, hydroxyl, amine and azide.

15. The method of claim 11, wherein $R^1$ and $R^2$ of formula (II) consist of structure (III):

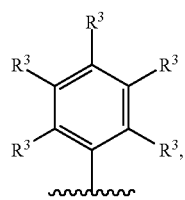

(III)

wherein $R^3$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone.

16. The method of claim 11, wherein $R^1$ and $R^2$ of formula (II) consist of structure (IV):

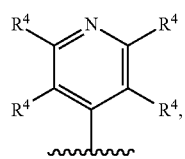

(IV)

wherein $R^4$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone.

17. The method of claim 11, wherein $R^1$ and $R^2$ of formula (II) consist of structure (V):

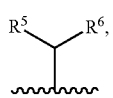

(V)

wherein $R^5$ and $R^6$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone.

18. The method of claim 11, wherein $R^1$ and $R^2$ of formula (II) consist of structure (VI):

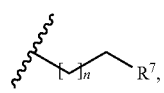

(VI)

wherein $R^7$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone; and n is an integer in the range from 0 to 18.

19. The method of claim 11, wherein $R^1$ and $R^2$ of formula (II) consist of structure (VII):

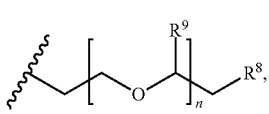

(VII)

wherein $R^8$ is independently selected from a group consisting of hydrogen, halogen, $C_{1-18}$ alkyl, $C_{2-18}$ alkenyl, $C_{2-18}$ alkynyl, $C_{3-8}$ cycloalkyl, $C_{3-8}$ heterocycloalkyl $C_{5-20}$ aryl, $C_{5-20}$ heteroaryl, alcohol, aldehyde, ester, carboxylic acid, anhydride, carboxamide, amine, hydroxylamine, oxime, azide, cyano, ether, thiol, thioether, sulfoxide, and sulfone;

$R^9$ is selected from hydrogen and methyl; and n is an integer in the range from 0 to 18.

20. The method of claim 11, wherein the diazaperopyrenium dication of formula (II) is selected from a group consisting of formulas (VIII) to (XV):

(VIII)
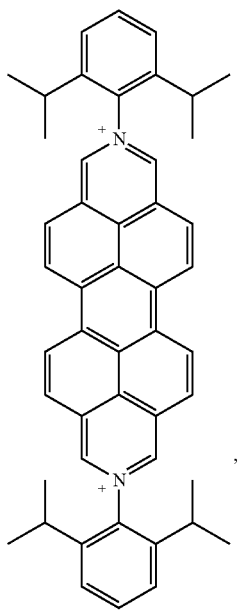
,
(IX)
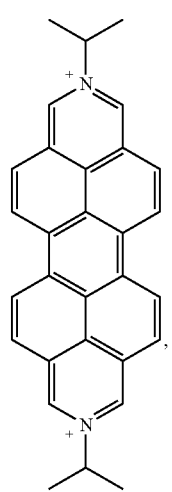
,
-continued
(X)
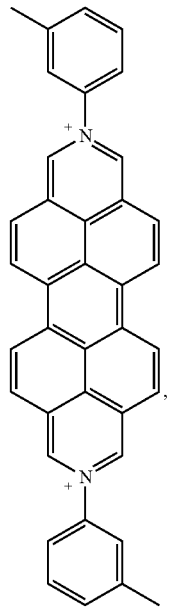
,
(XI)
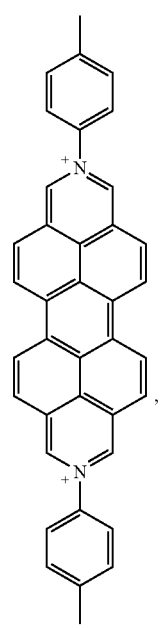
,